United States Patent [19]
Lang, Jr. et al.

[11] 4,141,992
[45] Feb. 27, 1979

[54] CYCLOALKYLCARBOXYAMIDINES AND HALOBENZAMIDINES AS ANTI-AMEBIC AGENTS

[75] Inventors: Stanley A. Lang, Jr., Stony Point; Yang-I Lin, Nanuet; Thomas L. Fields, Pearl River; Paul F. Fabio, Pearl River; Keith C. Murdock, Pearl River, all of N.Y.

[73] Assignee: American Cyanamid Company, Stamford, Conn.

[21] Appl. No.: 815,400

[22] Filed: Jul. 13, 1977

Related U.S. Application Data

[63] Continuation of Ser. No. 705,312, Jul. 14, 1976, abandoned, which is a continuation-in-part of Ser. No. 606,805, Aug. 22, 1975, abandoned.

[51] Int. Cl.$^2$ .................. A61K 31/155; C07C 123/00
[52] U.S. Cl. .......................... 424/326; 260/564 RF; 260/239 A; 260/326.5 J; 424/244; 424/267; 424/274; 546/204; 546/190

[58] Field of Search .......................... 260/378; 424/326

[56] References Cited

U.S. PATENT DOCUMENTS

| | | | |
|---|---|---|---|
| 3,184,482 | 5/1965 | Steiger | 260/378 |
| 3,654,319 | 4/1972 | Neeff | 260/378 X |
| 3,960,947 | 6/1976 | Duerr et al. | 260/558 R X |
| 3,972,932 | 8/1976 | Panneman | 260/558 R X |
| 4,078,086 | 3/1978 | Winkelmann et al. | 424/326 |

FOREIGN PATENT DOCUMENTS 540870 10/1955 Belgium .......................... 260/564 RF Primary Examiner—Allen B. Curtis
Attorney, Agent, or Firm—Claude J. Caroli

[57] ABSTRACT 2,6 Anthraquinonylene cycloalkylcarboxamidines and halobenzamidines that are effective against cecal and hepatic amebic infestations in warm-blooded animals, methods of treatment therewith and therapeutic compositions thereof.

13 Claims, No Drawings

CYCLOALKYLCARBOXYAMIDINES AND HALOBENZAMIDINES AS ANTI-AMEBIC AGENTS

CROSS REFERENCE TO RELATED APPLICATIONS

This application is a continuation of our co-pending application Ser. No. 705,312, filed July 14, 1976, now abandoned, which in turn is a continuation-in-part of our prior application, Ser. No. 606,805, filed Aug. 22, 1975, and now abandoned.

DESCRIPTION OF THE PRIOR ART

U.S. Pat. No. 3,184,482 discloses a compound of the formula:

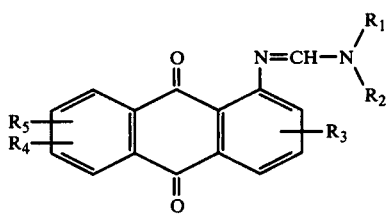

wherein $R_1$ and $R_2$ are hydrogen or lower alkyl and $R_3$, $R_4$ and $R_5$ are hydrogen, hydroxy or

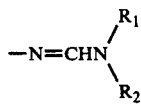

Utility is described as antibacterial, antiviral, antiprotazoal and anthelmintic.

BRIEF SUMMARY OF THE INVENTION

This invention discloses novel compounds of the formula:

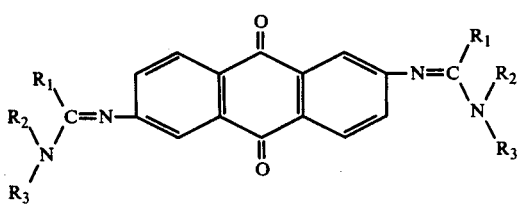

wherein $R_1$ is selected from the group consisting of hydrogen, alkyl having from 1-4 carbon atoms and cycloalkyl having from 3-6 carbon atoms; wherein $R_2$ and $R_3$ are each individually selected from the group consisting of hydrogen and alkyl having from 1-4 carbon atoms; wherein $R_1$ and $R_2$ taken together is selected from the group consisting of trimethylene, tetramethylene and pentamethylene; and pharmaceutically acceptable salts there of.

This invention is also concerned with the method of treating cecal and hepatic amebic infections in warm-blooded animals with the above compounds.

DETAILED DESCRIPTION OF THE INVENTION

The compounds of the present invention are normally crystalline solids being soluble in dimethylformamide and dimethylsulfoxide and less soluble in chloroform, alcohol and acetone. The salts (mono and di) are readily soluble in water and less soluble in alcohol.

The compounds of the present invention may be prepared according to the following methods:

(A) 2,6-Diaminoanthraquinone (1mole) is reacted with a complex formed from phosphorous oxychloride (1.5 to 3 moles) and an N,N-dialkylamide or N-alkylamide (2 to 6 or more moles) in a solvent such as acetonitrile (at a ratio of about 1-3 liters of solvent per mole of amine) at a temperature of 25° to 70° C. for a period of about one to 24 hours.

More specifically, to a solution of the N,N-dialkylamide or N-alkylamide in the solvent is added phosphorous oxychloride at −5° to 20° C. The resulting mixture is stirred at 0° to room temperature for 30 minutes to 6 hours. The 2,6-diaminoanthraquinone is added and the reaction mixture is stirred at 25° to 70° C. for one to 24 hours. The reaction mixture is then poured into ice water and basified. The resulting crystals are collected by filtration and recrystallized from an appropriate solvent or mixture or solvents such as chloroform/hexane.

(B) 2,6-Diaminoanthraquinone (1 mole) is reacted with a 1-aza-2-methoxy-1-cycloalkene (2 to 5 or more moles) in a solvent such as dimethylacetamide or dimethylformamide at a ratio of about one liter of solvent per mole of amine and acetic acid at a ratio of about 2 moles per mole of amine at reflux temperature for a period of one to 12 hours. The addition of ether to the reaction mixture causes the precipitation of the product which is collected and recrystallized as in (A).

(C) 2,6-Dimanoanthraquinone (72 parts) is slurried in 300 parts of a triethyl ortho acid and 250 parts of acetic anhydride is added. The mixture is refluxed for one to 8 hours, cooled and the solid product is collected, washed and dried. Purification is accomplished by dissolving this crude product in 1000 parts of chloroform, filtration and concentration of the filtrate. Further purification may be realized by recrystallization from a solvent such as dimethylformamide. A bis-imino-ether (8 parts) is slurried in 45 parts of an appropriate amine. One equivalent of glacial acetic acid for each part of imino-ether is added and the slurry is heated in an oil bath at 100°–160° C. for 8 to 24 hours. (The use of a bomb is recommended with low boiling amines). The reaction mixture is cooled. Products which crystallize are collected and recrystallized from a solvent such as methanol, ethanol, methyl cellusolve or dimethylformamide. For products which do not crystallize, the volatiles are removed in vacuo and the residue is dissolved in methanol. Upon cooling the product crystallizes and is recrystallized from a suitable solvent as above.

(D) Diethyl N,N'-(2,6-anthraquinonylene) di-formimidate is combined with at least 2 molar equivalents of primary or secondary amine and heated at a temperature of 130°–200° C. for 2 to 18 hours. The reaction mixture is stripped of volatiles under reduced pressure and the pure product is obtained by recrystallization from a suitable solvent.

(E) Diaminoanthraquinone is combined with 2 or more molar equivalents of dialkylamide dialkylacetal with or without the corresponding amide as solvent. The mixture is heated at 130°–150° C. for 2 to 66 hours. The reaction mixture is stripped of volatiles under reduced pressure. The residue is washed with hexane and the product is obtained by recrystallization from a suitable solvent.

(F) Diaminoanthraquinone is combined with 2 or more molar equivalents of an amide. To this mixture is added at least 2 equivalents of an aryl sulfonyl halide. The mixture is heated at below 100° C. for 2 to 3 hours. Alcohol is added to the reaction mixture. The insoluble salt is collected and treated with an aqueous base to obtain the free base. Recrystallization from a suitable solvent gives the purified product.

The compounds of the present invention are active in treating cecal and hepatic amebic infections in warm-blooded animals. Two tests which establish this activity are as follows:

Organism

The organism used in both tests is the National Institute of Health 200μ strain of Entamoeba histolytica. This strain and an unidentified fecal flora are cultured in Cleveland-Collier Medium at 37° C. This medium consists of a liver infusion agar base overlaid with a horse serum:saline mixture (1:6) to which is added a few milligrams of sterile rice powder. The amebas are transferred to fresh media twice weekly.

Cecal Infections in Female Albino Wistar Rats

Pooled overlay (0.25 ml) of containing large numbers of amebas is injected into the cecums of anesthetized weanling rats during laparotomy. Treatment is begun on the day after inoculation. The compounds are dissolved or suspended in 0.2% aqueous agar and administered once daily, by gavage, for 5 consecutive days. Six days after inoculation of the amebas, the rats are sacrificed and a scraping from the cedal wall of each rat is mixed with a drop of 0.85% saline an examined microscopically for amebas. A rat is considered cured if no amebas are seen. The cure or clearance rate (number cured/number treated) for each regimen is calculated and corrected for non-specific cures observed in the untreated infected controls. An active dose is the lowest dose, in terms of mg/kg/day, which clears or cures 50% or more of the rats so treated. The results of typical compounds of the present invention appear in the following table together with results obtained using known effective drugs for comparison.

Hepatic Infections in Female Golden Hamsters

A piece of ameba-laden absorbable sponge, about 25 millimeters square, is inserted between the middle lobes of the livers of anesthetized hamsters during laparotomy. Untreated hamsters usually die from the resulting infection about 7 days after inoculation. Treatment is started on the day of inoculation as soon as the hamsters recover from the surgical anesthetic. The test compounds are dissolved or suspended in 0.2% aqueous agar and administered once daily, by gavage, for 5 consecutive days. Effective regimens prevent mortality. Survival rates are corrected for non-specific survival observed in untreated groups. An active dose is the lowest dose, expressed mg/kg/day, which protects 50% or more of the hamsters so treated as evidence by survival 14 days after inoculation. The results of typical compounds of the present invention appear in the following table together with the active dose of known effective drugs for comparison.

TABLE

| COMPOUNDS | CECAL INFECTION Lowest Active Dose mg/Kg/day | HEPATIC INFECTION Lowest Active Dose mg/Kg./day |
|---|---|---|
| N',N'''-(2,6-Anthraquinonylene)bis-N,N-dimethyl formamidine | 20 | 10 |
| N',N'''-(2,6-Anthraquinonylene)bis-N,N-diethyl acetamidine | 10 | 2.5 |
| N',N'''-(2,6-Anthraquinonylene)bis-N-octyl-N-methyl formamidine | 50 | — |
| N',N'''-(2,6-Anthraquinonylene)bis-N,N-diisopropyl formamidine | 20 | 100 |
| 2,6-Bis(piperidinomethyleneamino)-anthraquinone | 20 | 100 |
| 2,6-Bis[(1-piperidinopropylidene)-amino]anthraquinone | 50 | — |
| N',N'''-2,6-Anthraquinonylenebis-[N,N-dimethyl-p-chlorobenzamidine] | 20 | 50 |
| 2,6-Bis [1-(4-methylepiperidino)-ethylidene]amino anthraquinone | 10 | — |
| 6-n-Prpoyloxy-3-nitroimidazo[1,2-b]-pyridazine | 20 | 25 |
| 2-Methyl-5-nitroimidazole-1-ethanol | 10 | 10 |
| Nitrimidazine | 20 | 100 |
| Tinedazole | 5 | 25 |

The novel 2,6-anthraquinenylene amidines of the present invention are useful for ameliorating cecal and hepatic amebic infections in warm-blooded animals when administered in amounts ranging from about 0.5 mg. per kg. to about 40 mg. per kg. of body weight per day. A preferred dosage regimen for optimum results would be from about 2 mg. per kg. to about 29 mg. per kg. Thus, the daily dosage employed for a subject of about 70 kg. of body weight is about 35 mg. to about 2.8 g., and preferably about 140 mg. to about 2.0 g.

Suitable oral preparations consist, for example, of capsules, tablets, troches, suspensions, syrups and the like. In the case of tablets the principal active ingredient is mixed with conventional ingredients such as corn starch, lactose, sucrose, sorbitol, talc, stearic acid, magnesium stearate, dicalcium phosphate, gums or similar materials as nontoxic pharmaceutically acceptable diluents or carriers.

Sustained release formulations are also contemplated by the present invention.

The liquid forms in which the novel compositions of the present invention may be incorporated for administration include suitably flavored emulsions with edible oils, such as, cottonseed oil, sesame oil, coconut oil, peanut oil and the like, as well as elixirs and similar pharamceutucal vehicles. Sterile suspensions or solutions can be prepared for parenteral use. Isotonic preparations containing suitable perservatives are also desirable for injectable use.

EXAMPLE 1

N,N'-(2,6-Anthraquinonylene)-di-formimidic acid diethyl ester

A 35.7 g portion of 2,6-diaminoanthraquinone is mixed with 100 ml of triethylorthoformate containing 5 drops of concentrated H$_2$SO$_4$. The mixture is heated to reflux and the alcohol is removed as it forms over a 2 hour period. The reaction mixture is cooled to −10° C., the solid which forms is collected by filtration, washed with 2B alcohol and air dried. Recrystallization from dimethylformamide produces brown crystals, mp 235°–250° C.

EXAMPLE 2

N',N'''-2,6-Anthraquinonylenebis[N,N-dimethyl formamidine]

A suspension of 7.15 g of 2,6-diaminoanthraquinone in 17.68 g of N,N-dimethylformamide diethyl acetal is stirred and heated in an oil bath at 150° C. for 17 hours. The by-product, ethanol, distills out. A 30 ml portion of dimethylformamide is added and the hot mixture is filtered. The solid is washed with acetone giving red-brown rods. These rods are recrystallized from 30 ml of dimethylformamide and dried 4 hours at 80° C. giving a pale yellow solid.

EXAMPLE 3

N',N'''-2,6-Anthraquinonylenebis[N-propyl propionamidine]

A 60 g portion of propionyl chloride is added to a solution of 84.3 g of propylamine in 600 ml of ether at 0° C. The mixture is kept at room temperature overnight and filtered. The filtrate is concentrated under reduced pressure giving a yellow oil. This oil is distilled to give N-propylpropionamide as a colorless liquid.

To a solution of 34.5 g of N-propylpropionamide in 200 ml of acetonitrile is added 36.8 g of phosphorous oxychloride at 5°–10° C. The mixture is stirred at room temperature for one hour and then 23.8 g of 2,6-diaminoanthraquinone is added. The mixture is stirred for 6 hours at room temperature and then at 60° C. for 16 hours. The mixture is then poured into 1000 ml of ice-water and basified with 5N NaOH. The reddish orange crystals are collected by filtration, dissolved in chloroform and then filtered. The chloroform is evaporated under reduced pressure and the residue is recrystallized from 200 ml of 2-methoxy ethanol giving the product as purplish crystals, mp 193°–195° C.

EXAMPLE 4

N',N'''-2,6-Anthraquinonylenebis[N-propyl acetamidine]

To a solution of 99.2 g of propylamine in 600 ml of ether is added 60 g of acetyl chloride at 0° C. The reaction mixture is kept at room temperature overnight and then filtered. The filtrate is concentrated under reduced pressure giving a yellow oil which is distilled giving N-propyl acetamide as a colorless liquid.

A 23.8 g portion of 2,6-diaminoanthraquinone, 36.8 g of phosphorous oxychloride, 30.3 g of N-propylacetamide and 200 ml of acetonitrile are reacted as described in Example 1 giving the product as reddish crystals, mp 221°–224° C.

EXAMPLE 5

N',N'''-2,6-Anthraquinonylenebis[N-methyl propionamidine]

A 23.8 g portion of 2,6-diaminoanthraquinone, 36.8 g of phosphorous oxychloride, 26.1 g of N-methyl propionamide and 200 ml of acetonitrile are reacted as described in Example 1. The product is recrystallized from chloroform and hexane giving reddish crystals, m.p. 211°–213° C.

EXAMPLE 6

N',N'''-2,6-Anthraquinonylenebis[N-isopropyl acetamidine]

To a solution of 99.2 g of isopropylamine in 600 ml of ether is added 60 g of acetyl chloride at −10° in a methanol-ice bath. The reaction mixture is kept at room temperature for 4 hours and then filtered. The filtrate is concentrated under reduced pressure giving an oil. This oil is distilled giving N-isopropyl acetamide as a colorless oil.

A 23.8 g portion of 2,6-diaminoanthraquinone, 36.8 g of phosphorous oxychloride, 30.3 g of N-isopropyl acetamide and 200 ml of acetonitrile are reacted as described in Example 1 giving the product as orange crystals, m.p. 264°–267° C.

EXAMPLE 7

N',N'''-2,6-Anthraquinonylenebis [N-ethyl propionamidine]

A 120 g portion of ethylpropionate and 100 g of ethylamine are heated in a steel bomb for 2 hours at 140° C. The volatile materials are removed under reduced pressure at 40° C. The residue is distilled at a reduced pressure giving N-ethyl propionamide as a colorless oil.

A 23.8 g portion of 2,6-diaminoanthraquinone, 36.8 g of phosphorous oxychloride, 30.3 g of N-ethyl propionamide and 200 ml. of acetonitrile are reacted as described in Example 1 giving the product as reddish crystals, m.p. 213°–216° C.

EXAMPLE 8

N',N'''-2,6-Anthraquinonylenebis[N-isopropyl propionamidine]

To a solution of 84.3 g of isopropylamine in 600 ml of ether is added 60 g of propionyl chloride dropwise at −10° C. in a methanol-ice bath. The mixture is kept at room temperature for 4 hours and then filtered. The filtrate is concentrated under reduced pressure to an oil. This oil is distilled to give N-isopropyl propionamide as a colorless oil.

A 23.8 g portion of 2,6-diaminoanthraquinone, 36.8 g of phosphorous oxychloride, 34.5 of N-isopropyl propionamide and 200 ml of acetonitrile are reacted as described in Example 1 giving the product as reddish crystals, m.p. 235° C. -239° C.

EXAMPLE 9

N',N'''-2,6-Anthraquinonylenebis[N-methyl acetamidine]

A mixture of 21.8 g of N-methyl acetamide, 23.8 g of 2,6-diaminoanthraquinone, 36.8 g of phosphorous oxychloride and 200 ml of acetonitrile are reacted as described in Example 1 resulting in a brown crude product which is recrystallized from chloroform giving the product as orange crystals, mp. 266°–269° C.

EXAMPLE 10

N',N'''-2,6-Anthraquinonylenebis[N,N-diethyl acetamidine] 4,4'-methylenebis[3-hydroxy-2-naphthoate]

A 4.326 g portion of N',N'''-2,6-anthraquinonylenebis[N,N-diethyl acetamidine] and 3.884 g of pamoic acid are dissolved in 20 ml of dimethylformamide and then filtered. Ether is added causing the product to precipitate as yellow crystals of the pamoate salt, mp 253°–255° C.

EXAMPLE 11

N',N'''-2,6-Anthraquinonylenebis[N,N-dimethyl cyclopropanecarboxamidine]

To a solution of 300 ml of 40% aqueous dimethylamine in 500 ml of ether is added 52.0 g of cyclopropane carboxylic acid chloride in 100 ml of ether dropwise at 10°–25° C. The mixture is stirred at room temperature for 2 hours. A 50 ml portion of water is added. The ether layer is separated, washed with three 50 ml portions of water, dried over Na$_2$SO$_4$ and filtered. The ether is removed and the residue is distilled giving N,N-dimethyl cyclopropanecarboxamide as a colorless oil.

A 34.0 g portion of the above product, 23.8 g of 2,6-diaminoanthraquinone, 36.8 g of phosphorous oxychloride and 200 ml of acetonitrile are reacted as described in Example 1. Recrystallization from 2-methoxyethanol gives a product as orange crystals, m.p. 241–243° C.

EXAMPLE 12

N'N'''-2,6-Anthraquinonylenebis[N,N-diethyl cyclopropanecarboxamidine]

A 134 ml portion of diethylamine in 600 ml of ether and 52.0 g of cyclopropane carboxylic acid chloride are reacted as described in Example 14 giving N,N-diethyl-cyclopropanecarboxamide as a colorless oil.

A 42.4 portion of the above product, 23.8 g of 2,6-diaminoanthraquinone, 36.8 g of phosphorus oxychloride and 200 ml of acetonitrile are reacted as described in Example 1. Recrystallization from 2-methoxyethanol gives the product as orange crystals, mp 166°–168° C.

EXAMPLE 13

N',N'''-2,6-Anthraquinonylenebis propionamidine

A mixture of 72 g of 2,6-diaminoanthraquinone, 300 ml of triethyl orthopropionate and 250 ml of acetic anhydride is refluxed for 2 hours and then cooled in an ice bath. The solid is collected by filtration, washed with ether and dried. This solid is slurried in one liter of chloroform, filtered and the filtrate is treated with activated charcoal and filtered. This filtrate is concentrated in vacuo giving diethyl N,N'-anthraquinonylenebis propionamidate as an orange solid.

A 9.8 portion of ammonium bromide is dissolved in 100 ml of dimethylformamide. An 8.12 g portion of the above imino ether is added and the mixture is heated in an oil bath at 100° C. for 20 hours. The mixture is cooled to room temperature and the solid is collected by filtration and dried in vacuo at 80° C. This solid is slurried in 250 ml of water and filtered. The filtrate is basified with 1N NaOH. The solid is collected by filtration, washed with water and dried in vacuo. This solid is recrystallized from 20 ml of dimethylformamide and dried in vacuo at 80° C. giving the product as yellow crystals, mp 250°–252° C.

EXAMPLE 14

N',N'''-2,6-Anthraquinonylenebis[N,N-dimethyl cyclobutanecarboxamidine]

To a solution of 19.1 g of N,N-dimethyl cyclobutanecarboxylic acid amide in 150 ml. of acetonitrile was added 18.4 g of phosphorous oxychloride at 5°–10° C. The resulting mixture was stirred at room temperature for 1 hour. Then, 11.9 g of 2,6-diaminoanthraquinone was added. The mixture was stirred at 60° C. for 10 hours, poured into 600 ml of ice-water and then basified with 5N NaOH. Orange crystals were collected by filtration and washed with water. The crystals were dissolved in chloroform and filtered. The chloroform was removed under reduced pressure. Recrystallization of the residue from methyl cellusolve gave 16.2 g of orange crystals, mp 209°–211° C.

EXAMPLE 15

2,6-Bis[(1-methyl-2-pyrrolidinylidene amino]anthroquinone

To a solution of 34.5 g of 1-methyl-2-pyrrolidinone in 150 ml. of CH$_3$CN was added 18.4 g of phosphorous oxychloride at 5°–10° C. The mixture was stirred at room temperature for 1 hour. To the mixture was added 11.9 g of 2,6-diaminoanthraquinone. The resulting mixture was stirred at 60° C. for 10 hours, poured into 1000 ml of ice-water and basified with 5N NaOH. Reddish crystals thus obtained were collected by filtration and washed with water. Recrystallization from methyl cellusolve gave 14.0 g of reddish crystals, mp 267°–269° C.

EXAMPLE 16

N',N'''-2,6-Anthraquinonylenebis[N,N,2-trimethylpropionamidine]

To a solution of 23.3 g of N,N,2-trimethylproionamide in 150 ml of acetonitrite was added 36.8 g of phosphorous oxychloride at 5°–10° C. The resulting mixture was stirred at room temperature for 1 hour. Then 23.8 g of 2,6-diaminoanthraquinone was added. The mixture was stirred at 60° C. for 10 hours, poured into 600 ml of ice-water and then basified with 5N NaOH. Orange crystals were collected by filtration and washed with water. The crystals were dissolved in chloroform and filtered. The chloroform was removed under reduced pressure. Recrystallization of the residue from methyl cellusolve gave 8.0 g of orange crystals, mp 166°–168° C.

EXAMPLE 17

N',N'''-2,6-Anthraquinonylenebis[N-ethylacetamidine]

To a solution of 26.1 g. of N-ethylacetamide in 200 ml. of acetonitrile was added 36.8 g. of phosphorous oxychloride at 5°–10° C. The resulting mixture was stirred at room temerature for 1 hour. Then, 23.8 g. of 2,6-diaminoanthraquinone was added. The mixture was stirred at 60° C. for 10 hours, poured into 600 ml. of ice-water and then basified with 5N NaOH. Orange crystals were collected by filtration and washed with water. The orange crystals were dissolved in chloroform and filtered. The chloroform was removed under reduced pressure. Final recrystallization from a CHCl$_3$/hexane mixture gave 10.5 g. of orange crystals m.p. 271°–273° C.

EXAMPLE 18

N',N'''-2,6-Anthraquinonylenebis[N,N-diethyl-3-methylbutraamidine]

To a solution of 23.6 g. of N,N-diethyl-3-methylbutyramidine in 150 ml. of acetonitrile was added 18.4 g. of phosphorous oxychloride at 5°–10° C. The resulting mixture was stirred at room temperature for 1 hour. Then, 11.9 g. of 2,6-diaminoanthraquinone was added. The mixture was stirred at 60° C. for 10 hours, poured into 600 ml. of ice-water and basified with 5N NaOH. Reddish crystals were collected by filtration and washed with water. The crystals were dissolved in chloroform and filtered. The chloroform was removed under reduced pressure. Final recrystallization from methyl cellusolve gave 8.1 g of reddish crystals mp 167°–169° C.

EXAMPLE 19

N',N'''-2,6-Anthraquinonylenebis[N,N-3-trimethylbutyramidine]

To a solution of N,N-3-trimethylbutyramide in 150 ml of acetonitrile was added 18.4 g of phosphorous oxychloride at 5°–10° C. The resulting mixture was stirred at room temperature for 1 hour. Then, 11.9 g of 2,6-diaminoanthraquinone was added. The mixture was stirred at 60° C. for 10 hours, poured into 600 ml of ice-water and basified with 5N NaOH. Yellow crystals were collected by filtration and washed with water. The yellow crystals were dissolved in chloroform and filtered. The chloroform was removed under reduced pressure. Final recrystallization from methyl cellusolve gave 37 g of yellow crystals mp 180°–182° C.

EXAMPLE 20

N',N'''-2,6-Anthraquinonylenebis[N,N-diethylbutyramidine]

To a solution of 21.5 g of N,N-diethylbutyramide in 150 ml. of acetonitrile was added 10.8 ml. of phosphorous oxychloride at 5°–15° C. The mixture was stirred at room temperature for 1 hour. To the mixture was added 11.9 g. of 2,6-di-aminoanthraquinone. The resulting mixture was stirred at 60° C. for 10 hours, poured into 500 ml. of ice-water and basified with 5 N NaOH. Reddish crystals thus produced were collected by filtration and washed with water. Final recrystallization from a CHCl$_3$/methanol mixture gave 13.5 g. of reddish crystals, m.p. 145°–149° C.

EXAMPLE 21

N',N'''-2,6-Anthraquinonylenebis[N,N-diethyl]acetamidine succinate

A 4.33 g. portion of N',N'''-2,6-Anthraquinonylenebis-(N,N-diethyl)acetamidine in 100 ml. of chloroform and 1.18 g of succinic acid in 100 ml. of methanol were mixed. The resulting solution was evaporated under reduced pressure to dryness. The resulting yield was 5.5 g. of orange crystals m.p. 165°–166° C.

EXAMPLE 22

N',N'''-2,6-Anthraquinonylenebis[N,N-diethyl-3,3-dimethylpropionamidine]

To a solution of 23.6 g. of N,N-diethylpivalamide in 100 ml. of acetonitrile was added 18.4 g of phosphorous oxychloride at 5°–15° C. over a 30 minute period. The resulting mixture was stirred at room temperature for 30 minutes. Then 11.9 g. of 2,6-diaminoanthraquinone was added. The mixture was stirred at 60° C. for 20 hours then poured into 500 ml. ice-water. The mixture separated into oil and aqueous phases. The aqueous phase was decanted from the oil and filtered. The filtrate was basified with 75 ml. of 10N NaOH. Considerable solid was precipitated, collected, washed 3 times with water and dried to result in a product with melting point of 144° C.–146° C.

EXAMPLE 23

N',N'''-2,6-Anthraquinonylenebis[N,N-dimethylbutyramidine]

To a solution of 23.0 g. of N,N-dimethylbutyramide in 50 ml. of acetonitrile was added 30.7 g. of phosphorous oxychloride at 5°–15° C. over a 30 minute period. The resulting mixture was stirred at room temperature for 30 minutes. Then, 23.8 g. of 2,6-diaminoanthraquinone was added. The mixture was stirred at 60° C. for 20 hours poured into 500 ml. of ice-water and basified with 5N NaOH. Reddish crystals were dissolved in chloroform and filtered. The chloroform was removed under reduced pressure. Final recrystallization from methyl cellusolve gave 300 mg. of red powder m.p. 181°–184° C.

EXAMPLE 24

N',N'''-2,6-Anthraquinonylenebis[N,N-dimethyl-3-dimethylpropionamidine]

To a solution of 19.4 g of N,N-dimethylpivalamide in 100 ml of acetonitrile was added 18.4 g of phosphorous oxychloride at 5°–15° C. over a 30 minute period. The resulting mixture was stirred at room temperature for 30 minutes, and then heated in an oil bath at 60° C. for one hour. Then, 11.9 of 2,6-diaminoanthraquinone was added and the temperature of the oil bath was raised to 78° C. for 20 hours. Next, the mixture was poured into 500 ml of ice-water. The mixture separated into oil and aqueous phases. The aqueous phase was decanted from the oil and filtered. The filtrate was basified with 75 ml of 10N NaOH. Considerable solid was precipitated, collected and washed 3 times with water and dried to result in a product with a melting point, 158° C.–160° C.

EXAMPLE 25

N',N'''-2,6-Anthraquinonylenebis-[N,N-diethyl acetamidine]

To a solution of 276.0 g of dried N,N-diethylacetamide in 800 ml of acetonitrile, which is cooled in an ice-water bath to 5°–10° C., is added dropwise 87.4 ml of phosphorous oxychloride over a period of 10 to 15 minutes. The ice-water bath is removed and the resulting mixture is stirred at room temperature for one hour. A 95.2 g portion of 2,6-diaminoanthraquinone is added and the resulting mixture is stirred without heating for one hour and then at 60° C. for 7 ½ hours. The mixture is cooled to room temperature and is poured into 1000 ml of ice-water. The aqueous solution is diluted.

EXAMPLE 26

N,N'-2,6-Anthraquinonylenedi-acetimidic acid diethyl ester

A mixture of 35.7 g of 2,6-diaminoanthraquinone, 100 ml of triethylorthoacetate and 6 drops of concentrated sulfuric acid is heated for 6 hours in an oil bath At 130° C. with a take-off condenser and four inch Vigreux Column. A 5 ml portion of ethyl alcohol is collected, then the mixture is allowed to stir at room temperature overnight. An additional 60 ml of triethylorthoacetate is added, the mixture is refluxed for 6 hours longer and is allowed to stir overnight at room temperature. The brownish solid collected by filtration is washed with ether and dried in vacuo. A 10 g portion of the above product is recrystallized from 400 ml of methyl cellosolve, the solid is filtered and washed twice with ether and is dried in vacuo at 50° C. to give orange-tan crystals.

A 1.0 g portion of the brownish solid previously described is recrystallized from 100 ml of dimethylformamide to give orange crystals after drying in vacuo at 50° C. The recrystallized materials are combined to give the final product, mp 195°-197° C.

EXAMPLE 27

N',N'''-2,6-Anthraquinonylenebis[N,N-dimethyl acetamidine]

To a mixture of 5.96 g of 2,6-diaminoanthraquinone and 20 ml of N,N-dimethylacetamide is added 14.3 g of p-toluene sulfonyl chloride. The material is then heated on a steam bath for 2 hours with a color change from red to brown. A 100 ml portion of 2B ethyl alcohol is added, the solution is heated to boiling and filtered. The filtrate is cooled at −10° C. The solid collected is then washed with 2B alcohol. The solid is slurried in hot water, filtered while hot, and the insoluble solids washed twice with hot water. The filtrate and washes are basified with NaOH. The orange solid is dried, recrystallized from 2B alcohol and dried at 78° C. under vacuum with $P_2O_5$, mp 295°-330° C.

EXAMPLE 28

N,N'-2,6-Anthraquinonylenedi-propionimidic acid diethyl ester

A mixture of 7.2 g of 2,6-diaminoanthraquinone, 30 ml of triethylortho propionate and 25 ml of acetic anhydride is refluxed for 2 hours. The mixture is cooled to room temperature and a solid is collected by filtration then is washed with diethyl ether and dried in vacuo. The product is recrystallized from dimethyl formamide to give orange crystals, mp 195°-198° C.

EXAMPLE 29

N',N'''-2,6-Anthraquinonylenebis-[N,N-diethyl acetamidine]dihydrochloride

A portion of N',N'''-(2,6-anthraquinonylene)bis-N,N-diethyl acetamidine is suspended in methyl alcohol and methanolic HCl is added with stirring until solution is achieved, diethyl ether is added until cloudiness develops. The solution is kept at 0° C. overnight then is filtered. The precipitate collected is the dihydrochloride salt of N',N'-(2,6-(anthraquinonylene)bis-N,N-diethylacetamidine.

EXAMPLE 30

N',N'''-2,6-Anthraquinonylenebis(N-butyl-N-methyl)-propionamidine

A mixture of 8.12 g of N,N'-2,6-anthraquinonylenedi-propionimidic acid diethyl ester, 45 ml of N-methyl butylamine and 2.35 ml of acetic acid is heated at 130° C. in an oil bath with a reflux condenser for 18 hours. The reaction mixture is cooled to room temperature and filtered. The filtrate is concentrated in vacuo to a dark brown syrup which is taken up in 30 ml of methanol and is stored in a freezer. After 2 hours the orange crystals are filtered and washed with a small amount of methanol and dried in vacuo. The product is then recrystallized from 30 ml of methanol to give yellow crystals, mp 80°-82° C.

EXAMPLE 31

N',N'''-2,6-Anthraquinonylenebis[N,N'-dimethylpropionamidine]

To a solution of 24.2 g of N,N-dimethylpropionamide in 200 ml of acetonitrile, which is cooled in an ice-water bath to 5°-15° C. is added dropwise 21.6 ml of phosphorous oxychloride. The resulting mixture is stirred at room temperature for 30 minutes, then 23.8 g of 2,6-diaminoanthraquinone is added and stirring is continued at room temperature for 16 hours. The mixture is then stirred for 5 hours at 60° C. The reaction mixture is poured into one liter of ice-water, is stirred and is then filtered through a sintered glass funnel. The material retained on the funnel is extracted repeatedly with water and the combined solution of filtrate and extracts is made basic with 5N sodium hydroxide. The orange cryytals formed are collected by filtration. The crystalline material is washed with water and air dried. The product is then recrystallized from methyl cellosolve to give orange crystals, mp 206°-209° C.

EXAMPLE 32

N',N'''-2,6-Anthraquinonylenebis[N,N-dimethyl-p-chlorobenzamidine]

To a stirred solution of 27.6 g of N,N-dimethyl-p-chlorobenzamide in 100 ml of acetonitrile cooled at 5°-15° C. in an ice-water bath is added 10.8 ml of phosphorous oxychloride over a 30 minute period. The ice-water bath is removed and stirring is continued at room temperature for 30 minutes, then 11.9 g of 2,6-diaminoanthraquinone is added and stirring is continued at room temperature for one hour, then at 60° C. for 20 hours. The reaction mixture is then cautiously poured into a mixture of 500 ml of ice-water and stirring is continued for one hour gradually adding 75 ml of 10N sodium hydroxide. The orange solid is collected by filtration, is washed with water and is dried in vacuo at 80° C. The dried material is slurried in 300 ml of chloroform and is filtered. The filtrate is washed 2 times with water, is dried over magnesium sulfate, is filtered and concentrated in vacuo to a syrup. This material is slurried with 25 ml of methyl alcohol and the red crystals formed are collected by filtration. The product is washed with diethyl ether and is dried in vacuo, mp 296°-298° C.

EXAMPLE 33

N',N'''-2,6-Anthraquinonylenebis[N,N-dimethyl-p-fluorobenzamidine]

To a stirred solution of 32.8 g of N,N-dimethyl-p-chlorobenzamide in 133 ml of acetonitrile cooled at 5°-15° C. in an ice-water bath is added 14.7 ml of phosphorous oxychloride over a 30 minute period. The ice-water bath is removed and stirring is continued at room temperature for one hour, then at 60° C. for 20 hours. The reaction mixture is then cautiously poured into a mixture of 500 ml of ice water and stirring is continued for one hour gradually adding 75 ml of 10N sodium hydroxide. The reddish orange solid is collected by filtration, washed with water and dried in vacuo at 80°

C. The dried material is slurried in 300 ml of chloroform and filtered. The filtrate is washed 2 times with water, dried over magnesium sulfate, filtered and concentrated in vacuo to a syrup. This material is slurried with 25 ml of methyl alcohol and the crystals formed are collected by filtration. The product is washed with diethyl ether and dried in vacuo, mp 286°–289° C.

EXAMPLE 34

N',N'''-[2,6-Anthraquinonylenebis(nitriloethylidyne)]- bis N-isopropylacetamide

A suspension of 2.8 g of N',N'''-2,6-anthraquinonylenebis-[N-isopropylacetamidine] in 15 ml acetic anhydride was stirred at 120° C. until solution was achieved. The solution was filtered to yield 2.1 g of yellow crystals m.p. 141°–143° C.

We claim:

1. A compound of the formula:

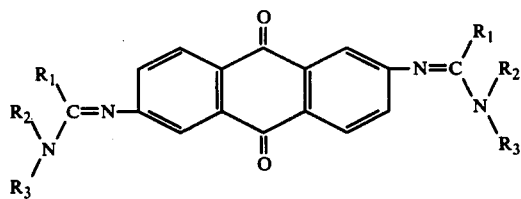

wherein $R_1$ is cycloalkyl having from 3–6 carbon atoms; wherein $R_2$ and $R_3$ are each individually selected from the group consisting of hydrogen and alkyl having from 1–4 carbon atoms; and pharmaceutically acceptable salts thereof.

2. The compound according to claim 1, N',N'''-2,6-anthraquinonylenebis[N,N-diethyl cyclopropanecarboxamidine].

3. The compound according to claim 1, N',N'''-2,6-anthraquinonylenebis[N,N-dimethyl cyclobutanecarboxamidine].

4. The compound according to claim 1, N',N'''-2,6-anthraquinonylenebis[N,N-dimethyl cyclopropanecarboxamidine].

5. The compound, N',N'''-2,6-anthraquinonylenebis-[N,N-dimethyl-p-chlorobenzamidine].

6. A method of treating cecal and hepatic amebic infections in warm-blooded animals which comprises administering to said animals an amount effective against said infections of a compound of the formula:

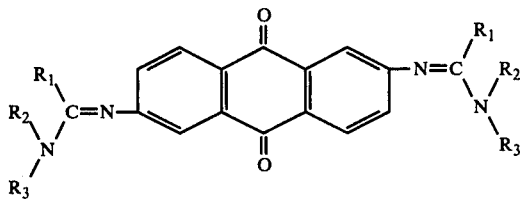

wherein $R_1$ is cycloalkyl having from 3–6 carbon atoms; wherein $R_2$ and $R_3$ are each individually selected from the group consisting of hydrogen and alkyl having from 1–4 carbon atoms; and pharmaceutically acceptable salts thereof.

7. The method according to claim 6, wherein the compound is N',N'''-2,6-anthraquinonylenebis[N,N-diethyl cyclopropanecarboxamidine].

8. The method according to claim 6, wherein the compound is N', N'''-2,6-anthraquinonylenebis[N,N-dimethyl cyclobutanecarboxamidine].

9. The method according to claim 6, wherein the compound is N',N'''-2,6-anthraquinonylenebis[N,N-dimethyl cyclopropanecarboxamidine].

10. A method of treating cecal and hepatic amebic infections in warm-blooded animals which comprises administering to said animals an amount effective against said infections of N',N'''-2,6-anthraquinonylenebis[N,N-dimethyl-p-chlorobenzamidine].

11. A therapeutic composition in unit dosage form which is useful for ameliorating cecal and hepatic amebic infections in warm-blooded animals comprising a compound of the formula:

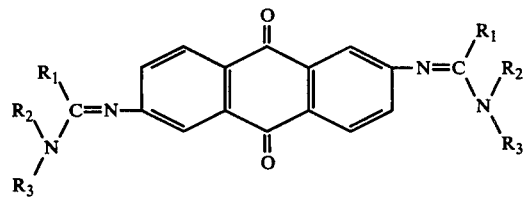

wherein $R_1$ is cycloalkyl having from 3–6 carbon atoms; wherein $R_2$ and $R_3$ are each individually selected from the group consisting of hydrogen and alkyl having from 1–4 carbon atoms; and pharmaceutically acceptable salts thereof in concentrations per dosage unit sufficient to provide a daily dosage of from about 140 mg. to about 2.0 g and a pharmaceutical carrier.

12. A therapeutic composition in unit dosage form which is useful for ameliorating cecal and hepatic amebic infections in warm-blooded animals comprising N',N'''-2,6-anthraquinonylenebis[N,N-dimethyl-p-chlorobenzamidine]and pharmaceutically acceptable salts thereof in concentrations per dosage unit sufficient to provide a daily dosage from about 140 mg to about 2.0 g and a pharmaceutical carrier.

13. The compound, N',N'''-2,6-anthraquinonylenebis[N,N-dimethyl-p-fluorobenzamidine].

* * * * *